United States Patent

Buckin et al.

[11] Patent Number: 5,983,723
[45] Date of Patent: Nov. 16, 1999

[54] ULTRASONIC MEASUREMENT EQUIPMENT WITH AT LEAST ONE NON-PIEZOELECTRIC RESONATOR CHAMBER BODY AND OUTER ELECTROACOUSTIC TRANSDUCERS

[75] Inventors: Vitaly Buckin, Ashfield Park 7A, Stillorgan Road, Dublin 4, Ireland; Leo De Maeyer; Theodor Funck, both of Göttingen, Germany

[73] Assignee: Vitaly Buckin, New York, N.Y.

[21] Appl. No.: 08/535,147

[22] PCT Filed: Apr. 22, 1994

[86] PCT No.: PCT/EP94/01265

§ 371 Date: Mar. 6, 1997

§ 102(e) Date: Mar. 6, 1997

[87] PCT Pub. No.: WO94/24526

PCT Pub. Date: Oct. 27, 1994

[30] Foreign Application Priority Data

Apr. 22, 1993 [DE] Germany ............... 43 13 216

[51] Int. Cl.$^6$ ............... G01N 29/00
[52] U.S. Cl. ............... 73/633; 73/634; 73/579
[58] Field of Search ............... 73/570, 584, 596, 73/597, 579, 641, 644, 23.2, 24.01, 52, 634, 633, 590, 592; 210/748; 310/334, 336

[56] References Cited

U.S. PATENT DOCUMENTS

| 3,974,405 | 8/1976 | Schussler et al. | 310/320 |
| 3,974,681 | 8/1976 | Namery | 73/600 |
| 4,607,520 | 8/1986 | Dam | 73/19.03 |
| 4,936,143 | 6/1990 | Schutten et al. | 73/597 |
| 4,949,584 | 8/1990 | Lade et al. | 73/865.8 |
| 5,141,331 | 8/1992 | Oehler et al. | 374/118 |
| 5,351,527 | 10/1994 | Blackburn et al. | 73/52 |

*Primary Examiner*—Michael Brock
*Assistant Examiner*—Richard A. Moller
*Attorney, Agent, or Firm*—Iandiorio & Teska

[57] ABSTRACT

The present invention relates to ultrasonic resonators comprising a resonator chamber body (11) and one or more electroacoustic transducers (13, 14). The resonator body consists of a non-piezoelectric material; it forming a resonant cavity for accommodating a specimen. This resonant cavity is configured so that between the acoustically excited internal walls a resonant wave field of standing linear acoustic waves is formed. The electroacoustic transducer(s) is(are) acoustically coupled externally to said resonator chamber body (FIG. 2) fixedly or removably or movably.

6 Claims, 1 Drawing Sheet von 21 → ... → nach 22

ULTRASONIC MEASUREMENT EQUIPMENT WITH AT LEAST ONE NON-PIEZOELECTRIC RESONATOR CHAMBER BODY AND OUTER ELECTROACOUSTIC TRANSDUCERS

FIELD OF THE INVENTION

The invention is based on an ultrasonic measurement apparatus and relates in particular to a device (termed ultrasonic resonator in the following), with the aid of which plane ultrasonic wave fields are generated in fluid specimens by means of electrical systems known in general (e.g. network analyzers) and with which the frequency dependency of the amplitude and/or the phase of these resonances may be analyzed. Such devices are employed mainly in determining the speed and absorption of sound by specimens in the ultrasound range.

DESCRIPTION OF THE RELATED ART

In known ultrasonic resonators the specimen is disposed directly between the highly precise parallel arrangement of the planar end surfaces of electroacoustic transducers. These transducers are inserted fluid-tight in openings of the walls of a cavity accommodating the specimen. This forms the so-called resonator cavity and the transducers form the acoustically active walls of the resonator in which the plane wave field materializes between the transducers.

one major problem, hitherto awaiting a satisfactory solution, as regards this known arrangement is securing the transducers in a highly accurate parallel position free of tension, but sealing the specimen. Especially in the case of aggressive specimen fluids this problem can hardly be solved. Apart from this, there is the risk of gas bubbles sticking persistently in the region of the seal with most of the sealing methods involved. The presence of such gas inclusions in the resonator heavily interfers with the propagation of the wave field.

SUMMARY OF THE INVENTION

The object of the present invention is thus based on providing ultrasonic measurement apparatuses having ultrasonic resonators in which the problem of sealing off the sound-active resonator wall is eliminated.

This object is achieved by an ultrasonic measurement apparatus having the characterizing features of claim 1.

Due to the ultrasonic transducers in the ultrasonic resonators of the present ultrasonic measurement apparatus being coupled externally (to an external side of the body containing the resonator cavity) acoustically to the resonator chamber body or specimen chamber body, no sealing problems whatsoever are encountered. Thus, the resonator chamber body may totally consist of a non-piezoelectric material and be produced from any suitable material. In the same way, the geometry of the internally located resonator cavity and the outer shape are restricted only by the acoustical requirements, it thus being possible e.g. to directly employ commercially available glass or quartz-glass cuvettes, as used in spectralphotometric applications.

Useful materials are all solid-stats materials resistant to the corresponding specimens. By suitably selecting the resonator chamber bodies according to their geometry (e.g. wall thickness) and their acoustical parameters the acoustic properties of the resonator calls thus formed may be optimized within broad limits and adapted to the requirements of the ultrasonic resonance measurement. In this way it is also easily possible to combine ultrasonic resonance measurements with other, e.g. optical, potentiometric, conductometric, etc. methods of analysis.

The transducers(s) of the present ultrasonic measurement apparatus is(are) preferably disposed movable, so that they may be moved, e.g. translatorically shifted or pivoted from a resting position, in which they are distant from the resonator chamber body, into a working position, in which they come into contact with the outside of the resonator chamber body. The transducers may also be applied durably to the external surfaces of the resonator chamber body (e.g. cuvettes for the measurement of light absorption or the fluorescence, flow cuvettes) and then replaced, together with the cuvettes as necessary. The transducers may be moved in a direction parallel to the plane active surface being formed by the transducers.

All transducers known in general (piezoelectric, capacitive, electrostatic) may be employed as the ultrasonic transducers. When employing piezoelectric transducers the sound-active surfaces may be improved in their acoustical properties by suitable coatings. In the same way, the acoustical properties of the resonator chamber by may be optimized by coating its surfaces.

On the surfaces of the acoustical transducers facing the resonator chamber body, electrically conducting electrodes are disposed which are connected to ground potential and simultaneously configured as an HF shield. Between this transducer surface and the surface of the resonator chamber body an optical acoustical contact needs to be assured. This may be achieved by a precise fit or by suitable coupling materials.

On the opposite surface of the transducers the HF electrodes are arranged, between which and the electronic emitter or receiver circuits a reliable electric contact needs to be produced.

Moving the transducers with respect to the surfaces of the resonator chamber body may be triggered automatically by inserting the body in the apparatus or by removing the body from the apparatus, thus facilitating cleaning operations and making a sterilization or exchange of the resonator chamber body as well as the use of disposable products possible.

BRIEF DESCRIPTION OF THE DRAWING

The invention will now be explained in more detail by disclosing further features and advantages of the invention, with reference to the drawing, in which.

DESCRIPTION OF THE PREFERRED EMBODIMENTS

Figure 1:
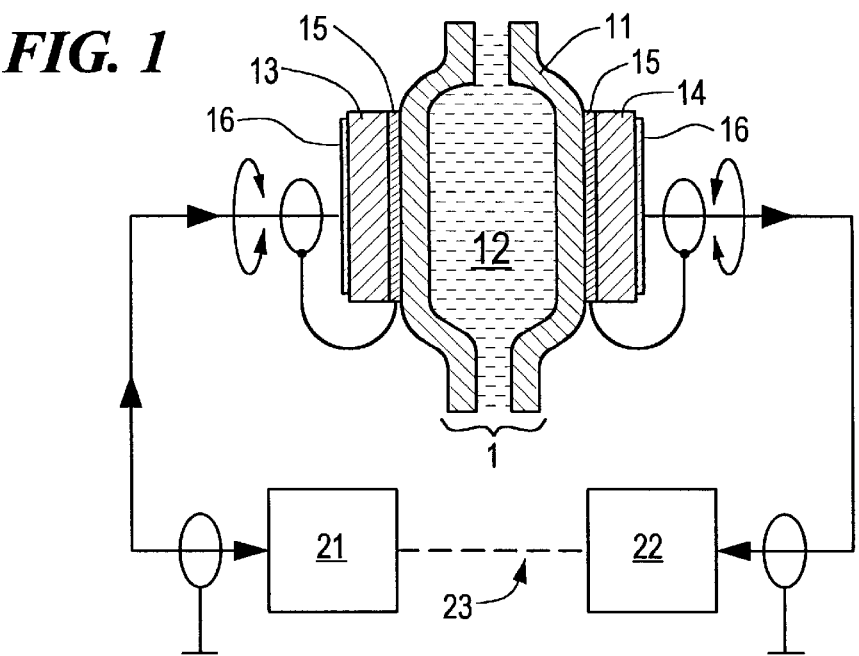
FIG. 1 is a schematic representation of an ultrasonic resonance apparatus including a resonator cell in accordance with the invention, the example of a resonator cell shown being that of one configured as a resonator cavity for flow Measurements.

The ultrasonic measurement apparatus depicted simplified in FIG. 1 contains a ultrasonic resonator cell 1 comprising a resonator chamber body 11, which in this case is configured as a flow cuvette, an emitter transducer 13 and a receiver transducer 14. In the interior of the resonator chamber body a resonator cavity 12 is located which is filled with the specimen in operation. At plane and parallel external surfaces of the resonator chamber body each of the transducers 13, 14 are acoustically coupled to the resonator chamber body via deposited metal coatings 15 connected to ground potential. HF transducer electrodes, also comprising deposited metal coatings, are located on their sides facing away from the resonator chamber body, they being connected to a conventional electronic measuring system 2 for electrical resonances, indicated merely in principle by an emitter system 21 and a receiver system 22 frequency-coupled (23) thereto.

Figure 2:
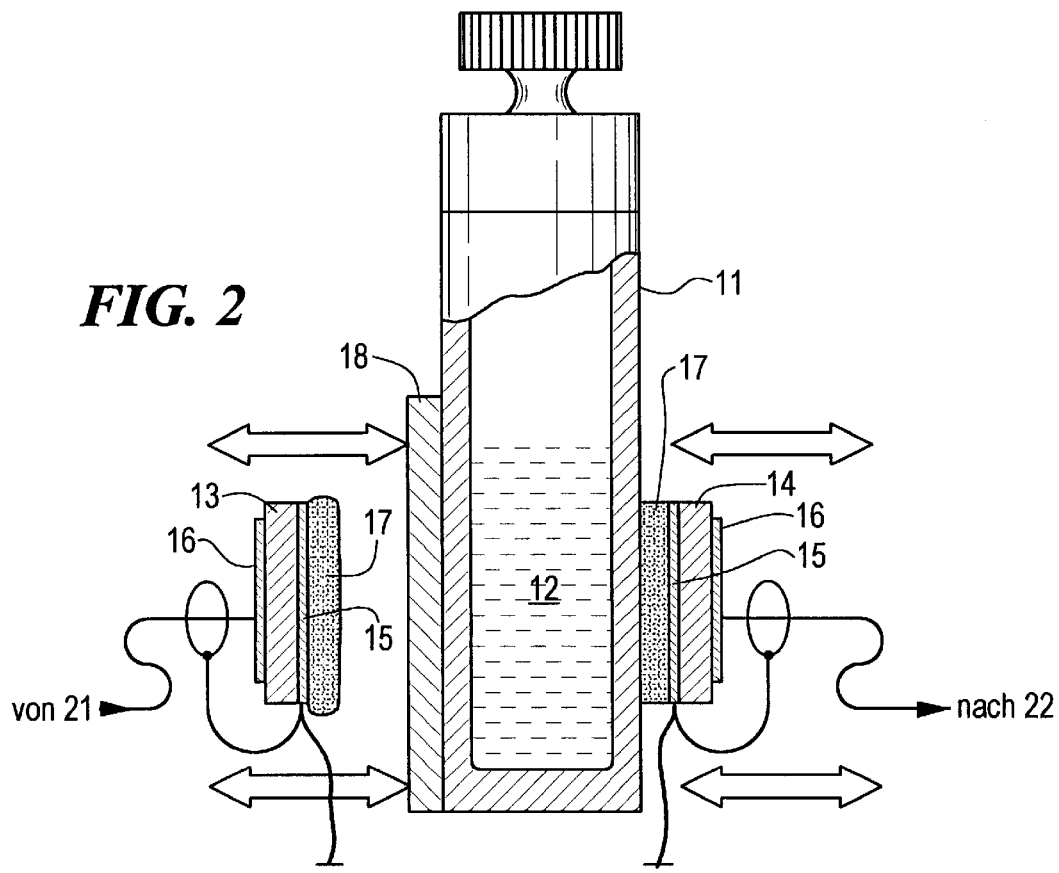
FIG. 2 is a schematic section view of a resonator arrangement having coatings for adapting impedance and movable transducers, the example of a resonator cell shown being here that of a commercially available glass cuvette for spectralphotometric analysis.

In FIG. 2 an ultrasonic resonator is depicted schematically, containing a spectralphotometer cuvette as the resonator chamber body 11. In this example the two transducers 13 and 14 are disposed movable. The receiver transducer 14 is shown in its working position, i.e. in acoustical contact with the external wall of the cuvette. Between receiver transducer and cuvette wall a coating 17 of material to improve the acoustic coupling is provided. On the side of the emitter transducer 13 shown in its resting position, i.e. distant from the cuvette, a coating 17 providing the acoustic contact is applied to the ground electrode 15 of the emitter transducer 13. Applied to the external surfaces of the cuvette is a coating 18 by which the acoustic impedance of the acoustically active interface is modified. Coatings of this kind, by which the acoustic impedance of an acoustically active surface or wall may be adapted to a desired value, are known and may be applied to all acoustically active or excited surfaces.

Mechanically shifting the transducers 13 and 14 between resting and working position may be achieved in various ways: a) manually mechanically, b) electromechanically or c) automatically on inserting or removing the cuvette.

The ultrasonic resonator may basically contain a means for thermostatic control (not shown in the drawing).

The characteristic acoustic properties of the ultrasonic resonator (resonant frequencies, half-value widths of the resonances and the like) are dictated by the fundamental frequency of the electroacoustic transducers, the acoustic properties of the specimen (speed of sound and attenuation of ultrasound by absorption, dispersion and the like) and by the geometry of the specimen. The acoustic properties of the specimen may be computed from the electrical properties of the resonator. In ultrasonic measurement apparatuses of the type as shown in FIG. 2 acoustic resonances may be generated at frequencies, for which a whole number of acoustic half waves precisely corresponds to the spacing of the two planoparallel acoustically emitter surfaces, include the specimens. The frequencies of the peak amplitude occuring at the receiver transducer are determined by the ultrasound speed and the half-value widths of the resulting resonances by the ultrasonic absorption.

The present ultrasonic measurement apparatus may include a plurality (e.g. circuited in parallel) of ultrasonic resonators of the kind described.

What is claimed is:

1. An ultrasonic measurement apparatus with an ultrasonic resonator for measuring the resonance of fluids in the ultrasonic range, said resonator having a resonator chamber body serving to accommodate a liquid specimen and forming a resonance cavity and including at least one electroacoustic transducer being coupled acoustically to the exterior wall of said chamber body, wherein each said electroacoustic transducer has a surface facing toward said resonator chamber body and on each of said surfaces, an electrically conducting electrode is attached, where said electrode is connected with a ground potential and in mechanical contact with said resonator chamber body, wherein each said electrode is acoustically adapted with said resonator chamber body by a precise geometrical fit or by an additional coating, wherein each said electroacoustic transducer is mounted movable between a working position with acoustic contact with said resonator chamber body and a resting position with distance therefrom.

2. The apparatus according to claim 1, wherein the surface of each said electroacoustic transducer is a plane active surface, each said transducer being shiftable in a direction parallel to said plane active surface.

3. The apparatus according to claim 1, wherein each said electroacoustic transducer is pivotally mounted.

4. The apparatus according to claim 1, wherein the exterior wall of the chamber body forms external surfaces where the acoustical coupling of each said transducer and its respective chamber body is achieved, said external surfaces being provided with coatings for adapting the acoustic impedance.

5. The apparatus according to claim 4, wherein, between each said electroacoustic transducer and it corresponding external surface of the chamber body, a coating of material suitable for improving the acoustic coupling is provided.

6. The apparatus according to claim 1, wherein the chamber body is insertable and removable into and from the apparatus, said transducers being automatically adjusted in response to the insertion of the chamber body into the apparatus.

\* \* \* \* \*